(12) United States Patent
Toy et al.

(10) Patent No.: US 11,229,798 B2
(45) Date of Patent: Jan. 25, 2022

(54) FIXATION FOR LEADLESS CARDIAC DEVICES

(71) Applicant: CARDIAC PACEMAKERS, INC., St. Paul, MN (US)

(72) Inventors: Peter Toy, Hugo, MN (US); Keith R. Maile, New Brighton, MN (US); Brendan Early Koop, Ham Lake, MN (US); Bryan J. Swackhamer, Shoreview, MN (US); Allan Charles Shuros, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 203 days.

(21) Appl. No.: 15/915,279

(22) Filed: Mar. 8, 2018

(65) Prior Publication Data
US 2018/0256902 A1    Sep. 13, 2018

Related U.S. Application Data

(60) Provisional application No. 62/469,740, filed on Mar. 10, 2017.

(51) Int. Cl.
*A61N 1/375* (2006.01)
*A61N 1/05* (2006.01)
(Continued)

(52) U.S. Cl.
CPC ............ *A61N 1/3756* (2013.01); *A61B 90/39* (2016.02); *A61N 1/057* (2013.01); *A61N 1/059* (2013.01);
(Continued)

(58) Field of Classification Search
CPC .. A61N 1/3756; A61N 1/37518; A61N 1/057; A61N 1/059; A61N 1/0573;
(Continued)

(56) References Cited

U.S. PATENT DOCUMENTS 4,301,815 A    11/1981  Doring
5,807,399 A     9/1998  Laske et al.
(Continued)

FOREIGN PATENT DOCUMENTS

EP    1957148 A1    8/2008
EP    2818201 B1    7/2016
(Continued)

OTHER PUBLICATIONS

International Search Report and Written Opinion dated May 28, 2018 for International Application No. PCT/US2018/021741.

*Primary Examiner* — Mallika D Fairchild
(74) *Attorney, Agent, or Firm* — Seager, Tufte & Wickhem LLP

(57) ABSTRACT

An implantable leadless pacing device and delivery system may comprise an implantable leadless pacing device and a catheter configured to deliver the implantable leadless packing device to a target location. The implantable device may comprise a power source, circuitry operatively coupled to the power source, a housing at least partially enclosing the circuitry, a first electrode secured relative to and offset from a longitudinal axis of the housing and exposed exterior to the housing, and a fixation mechanism secured relative to the housing. The fixation mechanism may comprise at least one tine configured to move between an elongated delivery configuration and a curved deployed configuration and radially offset from the first electrode. The catheter may comprise a distal holding section defining a cavity configured to receive the implantable leadless pacing device.

19 Claims, 10 Drawing Sheets

(51) Int. Cl.
*A61N 1/365* (2006.01)
*A61B 90/00* (2016.01)
*A61M 31/00* (2006.01)
*A61M 25/00* (2006.01)

(52) U.S. Cl.
CPC .. *A61N 1/37518* (2017.08); *A61B 2090/3925* (2016.02); *A61B 2090/3966* (2016.02); *A61M 25/0074* (2013.01); *A61M 31/007* (2013.01); *A61N 1/0573* (2013.01); *A61N 1/365* (2013.01); *A61N 1/37516* (2017.08)

(58) Field of Classification Search
CPC .... A61N 1/365; A61N 1/37516; A61B 90/39; A61B 2090/3925; A61B 2090/3966; A61M 25/0074; A61M 31/007
See application file for complete search history.

(56) References Cited

U.S. PATENT DOCUMENTS

| | | | |
|---|---|---|---|
| 5,908,381 A | 6/1999 | Aznoian et al. | |
| 6,181,973 B1 | 1/2001 | Ceron et al. | |
| 6,224,725 B1 | 5/2001 | Glocker | |
| 6,395,017 B1 | 5/2002 | Dwyer et al. | |
| 6,409,674 B1 | 6/2002 | Brockway et al. | |
| 6,497,803 B2 | 12/2002 | Glocker et al. | |
| 6,551,477 B2 | 4/2003 | Glocker et al. | |
| 6,582,441 B1 | 6/2003 | He et al. | |
| 6,638,268 B2 | 10/2003 | Niazi | |
| 6,786,918 B1 | 9/2004 | Krivoruchko et al. | |
| 7,248,913 B2 | 7/2007 | Hassett | |
| 7,321,798 B2 | 1/2008 | Muhlenberg et al. | |
| 7,381,216 B2 | 6/2008 | Buzzard et al. | |
| 7,499,758 B2 | 3/2009 | Cates et al. | |
| 7,509,169 B2 | 3/2009 | Eigler et al. | |
| 7,608,099 B2 | 10/2009 | Johnson et al. | |
| 7,666,203 B2 | 2/2010 | Chanduszko et al. | |
| 7,678,081 B2 | 3/2010 | Whiting et al. | |
| 7,799,037 B1 | 9/2010 | He et al. | |
| 7,840,281 B2 | 11/2010 | Kveen et al. | |
| 7,937,161 B2 | 5/2011 | Hastings et al. | |
| 7,993,351 B2 | 8/2011 | Worley et al. | |
| 8,002,822 B2 | 8/2011 | Glocker et al. | |
| 8,010,209 B2 | 8/2011 | Jacobson | |
| 8,103,361 B2 | 1/2012 | Moser | |
| 8,185,213 B2 | 5/2012 | Kveen et al. | |
| 8,267,987 B2 | 9/2012 | Johnson et al. | |
| 8,352,028 B2 | 1/2013 | Wenger | |
| 8,364,280 B2 | 1/2013 | Marnfeldt et al. | |
| 8,382,813 B2 | 2/2013 | Shumer | |
| 8,428,750 B2 | 4/2013 | Kolberg | |
| 8,478,431 B2 | 7/2013 | Griswold et al. | |
| 8,504,156 B2 | 8/2013 | Bonner et al. | |
| 8,527,068 B2 | 9/2013 | Ostroff | |
| 8,532,790 B2 | 9/2013 | Griswold | |
| 8,548,605 B2 | 10/2013 | Ollivier | |
| 8,615,310 B2 | 12/2013 | Khairkhahan et al. | |
| 8,634,912 B2 | 1/2014 | Bomzin et al. | |
| 8,721,587 B2 | 5/2014 | Berthiaume et al. | |
| 8,727,996 B2 | 5/2014 | Mian et al. | |
| 8,758,365 B2 | 6/2014 | Bonner et al. | |
| 8,855,789 B2 | 10/2014 | Jacobson | |
| 8,894,824 B2 | 11/2014 | Glocker et al. | |
| 8,903,513 B2 | 12/2014 | Ollivier | |
| 8,926,588 B2 | 1/2015 | Berthiaume et al. | |
| 8,945,145 B2 | 2/2015 | Tran et al. | |
| 8,945,146 B2 | 2/2015 | Steingisser et al. | |
| 8,948,883 B2 | 2/2015 | Eggen et al. | |
| 8,958,892 B2 | 2/2015 | Khairkhahan et al. | |
| 9,020,611 B2 | 4/2015 | Khairkhahan et al. | |
| 9,072,872 B2 | 7/2015 | Asleson et al. | |
| 9,101,281 B2 | 8/2015 | Reinert et al. | |
| 9,119,959 B2 | 9/2015 | Rys et al. | |
| 9,126,032 B2 | 9/2015 | Khairkhahan et al. | |
| 9,155,882 B2 | 10/2015 | Grubac et al. | |
| 9,168,372 B2 | 10/2015 | Fain | |
| 9,204,842 B2 | 12/2015 | Mothilal et al. | |
| 9,205,225 B2 | 12/2015 | Khairkhahan et al. | |
| 9,216,293 B2 | 12/2015 | Berthiaume et al. | |
| 9,220,906 B2 | 12/2015 | Griswold et al. | |
| 9,238,145 B2 | 1/2016 | Wenzel et al. | |
| 9,242,102 B2 | 1/2016 | Khairkhahan et al. | |
| 9,272,155 B2 | 3/2016 | Ostroff | |
| 9,283,381 B2 | 3/2016 | Grubac et al. | |
| 9,283,382 B2 | 3/2016 | Berthiaume et al. | |
| 9,283,392 B2 | 3/2016 | Moore et al. | |
| 9,308,365 B2 | 4/2016 | Nordstrom et al. | |
| 9,308,374 B2 | 4/2016 | Kveen et al. | |
| 9,339,197 B2 | 5/2016 | Griswold et al. | |
| 9,351,648 B2 | 5/2016 | Mothilal et al. | |
| 9,358,387 B2 | 6/2016 | Suwito et al. | |
| 9,414,857 B2 | 8/2016 | Wood et al. | |
| 9,421,384 B2 | 8/2016 | Taff et al. | |
| 9,433,780 B2 | 9/2016 | Regnier et al. | |
| 9,446,248 B2 | 9/2016 | Sheldon et al. | |
| 9,463,315 B2 | 10/2016 | Bomzin et al. | |
| 9,468,773 B1 | 10/2016 | Anderson et al. | |
| 9,504,820 B2 | 11/2016 | Bonner et al. | |
| 9,511,236 B2 | 12/2016 | Varady et al. | |
| 9,517,336 B2 | 12/2016 | Eggen et al. | |
| 9,517,337 B2 | 12/2016 | Ollivier | |
| 9,526,522 B2 | 12/2016 | Wood et al. | |
| 9,526,891 B2 | 12/2016 | Eggen et al. | |
| 9,539,423 B2 | 1/2017 | Bonner et al. | |
| 9,555,236 B2 | 1/2017 | Regnier et al. | |
| 9,579,500 B2 | 2/2017 | Rys et al. | |
| 9,610,454 B2 | 4/2017 | Doan et al. | |
| 9,623,234 B2 | 4/2017 | Anderson | |
| 9,662,487 B2 | 5/2017 | Kveen et al. | |
| 9,675,798 B2 | 6/2017 | Grubac et al. | |
| 9,717,421 B2 | 8/2017 | Griswold et al. | |
| 9,724,507 B2 | 8/2017 | Wood et al. | |
| 9,750,931 B2 | 9/2017 | Wood et al. | |
| 9,764,139 B2 | 9/2017 | Christensen | |
| 9,775,982 B2 | 10/2017 | Grubac et al. | |
| 9,808,617 B2 | 11/2017 | Ostroff et al. | |
| 9,808,629 B2 | 11/2017 | Steingisser et al. | |
| 9,814,896 B2 | 11/2017 | Solem | |
| 9,833,625 B2 | 12/2017 | Waldhauser et al. | |
| 9,833,626 B2 | 12/2017 | Klimovitch et al. | |
| 9,844,659 B2 | 12/2017 | Grubac et al. | |
| 9,844,664 B2 | 12/2017 | McEvoy et al. | |
| 9,861,815 B2 | 1/2018 | Tran et al. | |
| 9,867,982 B2 | 1/2018 | Berthiaume et al. | |
| 2003/0078618 A1 | 4/2003 | Fey et al. | |
| 2005/0101984 A1 | 5/2005 | Chanduszko et al. | |
| 2005/0165472 A1 | 7/2005 | Glocker | |
| 2005/0209653 A1 | 9/2005 | Herbert et al. | |
| 2005/0267555 A1 | 12/2005 | Marnfeldt et al. | |
| 2006/0009737 A1 | 1/2006 | Whiting et al. | |
| 2006/0106442 A1 | 5/2006 | Richardson et al. | |
| 2009/0082828 A1 | 3/2009 | Ostroff | |
| 2010/0274227 A1 | 10/2010 | Khairkhahan et al. | |
| 2011/0112548 A1 | 5/2011 | Fifer et al. | |
| 2011/0270339 A1 | 11/2011 | Murray, III et al. | |
| 2011/0270340 A1 | 11/2011 | Pellegrini et al. | |
| 2012/0095539 A1 | 4/2012 | Khairkhahan et al. | |
| 2012/0109148 A1 | 5/2012 | Bonner et al. | |
| 2012/0172690 A1 | 7/2012 | Anderson et al. | |
| 2012/0172891 A1 | 7/2012 | Lee | |
| 2012/0172892 A1* | 7/2012 | Grubac | A61N 1/0573 606/129 |
| 2012/0271163 A1 | 10/2012 | Foster et al. | |
| 2013/0012925 A1 | 1/2013 | Berthiaume et al. | |
| 2013/0035636 A1 | 2/2013 | Beasley et al. | |
| 2013/0103047 A1 | 4/2013 | Steingisser et al. | |
| 2013/0253342 A1 | 9/2013 | Griswold et al. | |
| 2013/0253346 A1 | 9/2013 | Griswold et al. | |
| 2013/0267848 A1* | 10/2013 | Fearnot | A61B 8/12 600/439 |
| 2014/0018818 A1 | 1/2014 | Somogyi et al. | |
| 2014/0107723 A1* | 4/2014 | Hou | A61N 1/3756 607/28 |

(56) References Cited

U.S. PATENT DOCUMENTS

| | | |
|---|---|---|
| 2014/0324145 A1 | 10/2014 | Eggen et al. |
| 2014/0378991 A1 | 12/2014 | Ollivier |
| 2014/0379041 A1* | 12/2014 | Foster ............... A61N 1/37205 607/5 |
| 2015/0039070 A1 | 2/2015 | Kuhn et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051615 A1* | 2/2015 | Schmidt ............... A61N 1/3756 606/129 |
| 2015/0051616 A1 | 2/2015 | Haasl et al. |
| 2015/0051682 A1 | 2/2015 | Schmidt et al. |
| 2015/0094668 A1 | 4/2015 | Wood et al. |
| 2015/0094735 A1 | 4/2015 | Ward et al. |
| 2015/0283376 A1 | 10/2015 | Ollivier et al. |
| 2015/0306378 A1 | 10/2015 | Schmidt et al. |
| 2015/0306381 A1 | 10/2015 | Schmidt et al. |
| 2015/0335884 A1 | 11/2015 | Khairkhahan et al. |
| 2015/0352351 A1 | 12/2015 | Muessig et al. |
| 2016/0000563 A1 | 1/2016 | Asleson et al. |
| 2016/0007924 A1 | 1/2016 | Eigler et al. |
| 2016/0015287 A1 | 1/2016 | Anderson et al. |
| 2016/0015322 A1 | 1/2016 | Anderson et al. |
| 2016/0030107 A1* | 2/2016 | Herbst ............... A61B 18/1477 604/506 |
| 2016/0059003 A1 | 3/2016 | Eggen et al. |
| 2016/0067446 A1 | 3/2016 | Klenk et al. |
| 2016/0067447 A1 | 3/2016 | Paspa et al. |
| 2016/0067503 A1 | 3/2016 | Berthiaume et al. |
| 2016/0082270 A1 | 3/2016 | Mothilal et al. |
| 2016/0096001 A1* | 4/2016 | Eidenschink ........ A61N 1/3756 606/129 |
| 2016/0114156 A1 | 4/2016 | Haasl et al. |
| 2016/0114157 A1 | 4/2016 | Haasl et al. |
| 2016/0158560 A1 | 6/2016 | Moore et al. |
| 2016/0206872 A1 | 7/2016 | Wood et al. |
| 2016/0213919 A1 | 7/2016 | Suwito et al. |
| 2016/0220829 A1 | 8/2016 | Wood |
| 2016/0228715 A9 | 8/2016 | Bonner et al. |
| 2016/0235971 A1 | 8/2016 | Wood et al. |
| 2016/0243350 A9 | 8/2016 | Grubac et al. |
| 2016/0243355 A1 | 8/2016 | Wood |
| 2016/0263372 A1 | 9/2016 | Wood et al. |
| 2016/0271388 A1 | 9/2016 | Ollivier et al. |
| 2016/0279423 A1 | 9/2016 | Kelly et al. |
| 2016/0296761 A1 | 10/2016 | Doan et al. |
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1* | 4/2017 | McDonnell ........ A61N 1/37205 |
| 2017/0100582 A1* | 4/2017 | McEvoy ............... A61N 1/3756 |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143955 A1 | 5/2017 | Soltis et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |

FOREIGN PATENT DOCUMENTS

| | | |
|---|---|---|
| EP | 2658599 B1 | 10/2016 |
| EP | 2651502 B1 | 11/2016 |
| EP | 2771064 B1 | 1/2017 |
| EP | 2780077 B1 | 1/2017 |
| WO | 2005007228 A1 | 1/2005 |
| WO | 2005113061 A1 | 12/2005 |
| WO | 2012145104 A1 | 10/2012 |
| WO | 2016126465 A1 | 8/2016 |

* cited by examiner

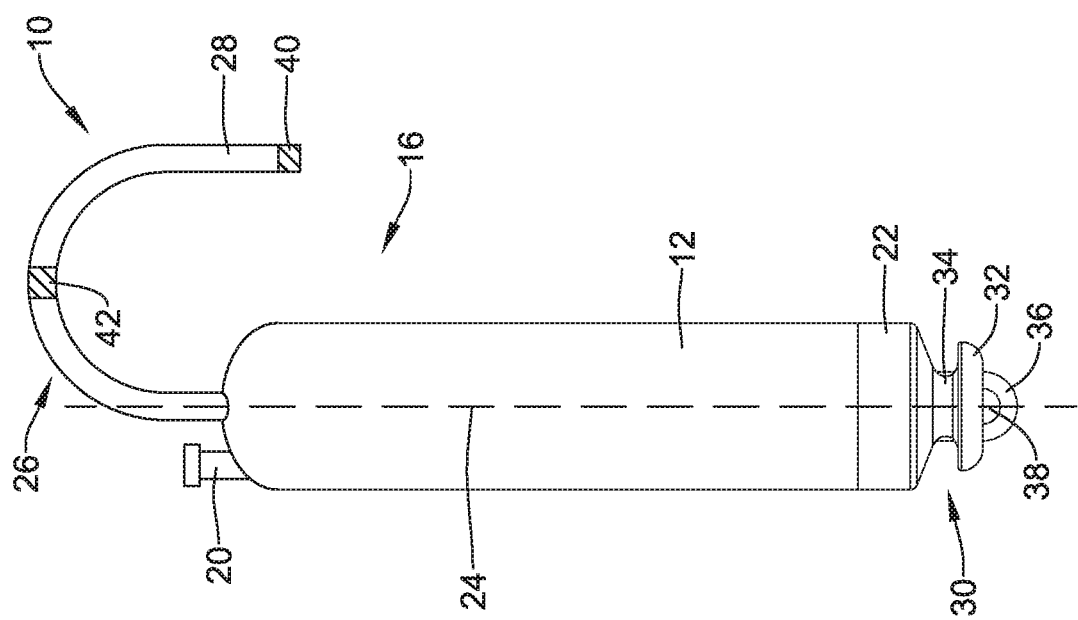

FIXATION FOR LEADLESS CARDIAC DEVICES

CROSS REFERENCE TO RELATED APPLICATIONS

The present application claims the benefit of and priority to U.S. Provisional Patent Application Ser. No. 62/469,740, filed Mar. 10, 2017, the disclosure of which is incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including delivery devices.

In a first example, an implantable leadless pacing device may comprise a power source, circuitry operatively coupled to the power source, the circuitry configured to pace a patient's heart and/or sense electrical activity of the patient's heart, a housing at least partially enclosing the circuitry, a first electrode secured to exposed exterior to the housing, and a fixation mechanism secured relative to the housing. The fixation mechanism may comprise a tine configured to move between an elongated delivery configuration and a curved deployed configuration and radially offset from the first electrode. When in the curved deployed configuration, the tine may be configured to curve away from the first electrode.

Alternatively or additionally to any of the examples above, in another example, the implantable leadless pacing device may further comprise an ultrasound marker positioned adjacent to a distal end of the at least one tine.

Alternatively or additionally to any of the examples above, in another example, a proximal end of the tine may be affixed to the housing generally in line with a longitudinal axis of the housing and the first electrode may be diametrically spaced from the tine.

In another example, an implantable leadless pacing device and delivery system may comprise an implantable leadless pacing device of any of the above examples and a catheter configured to deliver the implantable leadless pacing device to a target location. The catheter may comprise a distal holding section defining a cavity. The cavity may be configured to receive the implantable leadless pacing device.

Alternatively or additionally to any of the examples above, in another example, the system may further comprise an ultrasound marker positioned adjacent to a distal end of the tine.

Alternatively or additionally to any of the examples above, in another example, the tine may be configured to be in the elongated delivery configuration when the implantable leadless pacing device is disposed within the cavity of the distal holding section.

Alternatively or additionally to any of the examples above, in another example, the system may further comprise a radiopaque marker extending longitudinally along a wall of the distal holding section.

Alternatively or additionally to any of the examples above, in another example, the tine may be aligned with the radiopaque marker in the elongated delivery configuration.

Alternatively or additionally to any of the examples above, in another example, the system may further comprise a retention feature disposed within a cavity of the distal holding section, the retention feature may be configured to bias the at least one tine into the elongated delivery configuration.

Alternatively or additionally to any of the examples above, in another example, the retention feature may comprise a plurality of flexible fingers extending from an inner surface of the distal holding section.

Alternatively or additionally to any of the examples above, in another example, the tine may be configured to function as an electrically active element.

Alternatively or additionally to any of the examples above, in another example, the tine may comprise a conductive wire and a nitinol wire, the conductive wire and the nitinol wire positioned within an electrically insulating material.

Alternatively or additionally to any of the examples above, in another example, the system may further comprise a protrusion extending inwardly from an inner surface of the distal holding section and a groove extending longitudinally in the housing of the implantable device. When the implantable device is positioned within the distal holding section, the protrusion and the groove may be configured to mate such that the implantable device is in a predefined orientation.

Alternatively or additionally to any of the examples above, in another example, the retention feature may comprise a first end affixed to an inner wall of the distal holding section and a second free end configured to engage the tine.

Alternatively or additionally to any of the examples above, in another example, the free end of the retention feature may be configured to conform to an outer surface of the tine.

In another example, an implantable leadless pacing device may comprise a power source, circuitry operatively coupled to the power source, the circuitry configured to pace a patient's heart and/or sense electrical activity of the patient's heart, a housing at least partially enclosing the circuitry, a first electrode secured to exposed exterior to the housing, and a fixation mechanism secured relative to the housing. The fixation mechanism may comprise a tine configured to move between an elongated delivery configuration and a curved deployed configuration and radially offset from the first electrode. When in the curved deployed configuration, the tine may be configured to curve away from the first electrode.

Alternatively or additionally to any of the examples above, in another example, the implantable leadless pacing device may further comprise an ultrasound marker positioned adjacent to a distal end of the tine.

Alternatively or additionally to any of the examples above, in another example, the tine may be configured to function as an electrically active element.

Alternatively or additionally to any of the examples above, in another example, a proximal end of the tine may be affixed to the housing generally in line with a longitudinal axis of the housing and the first electrode may be diametrically spaced from the tine.

In another example, an implantable leadless pacing device and delivery system may comprise a implantable leadless pacing device as in any of the above examples and a catheter configured to deliver the implantable leadless pacing device to a target location. The catheter may comprise a distal holding section defining a cavity. The cavity may be configured to receive the implantable leadless pacing device.

Alternatively or additionally to any of the examples above, in another example, the system may further comprise an ultrasound marker positioned adjacent to a distal end of the tine.

Alternatively or additionally to any of the examples above, in another example, the tine may be configured to be in the elongated delivery configuration when the implantable leadless pacing device is disposed within the cavity of the distal holding section.

Alternatively or additionally to any of the examples above, in another example, the system may further comprise a radiopaque marker extending longitudinally along a wall of the distal holding section.

Alternatively or additionally to any of the examples above, in another example, the tine may be aligned with the radiopaque marker in the elongated delivery configuration.

Alternatively or additionally to any of the examples above, in another example, the system may further comprise a retention feature disposed within a cavity of the distal holding section, the retention feature may be configured to bias the tine into the elongated delivery configuration.

Alternatively or additionally to any of the examples above, in another example, the retention feature may comprise a plurality of flexible fingers extending from an inner surface of the distal holding section.

Alternatively or additionally to any of the examples above, in another example, the tine may be configured to function as an electrically active element.

Alternatively or additionally to any of the examples above, in another example, the tine may comprise a conductive wire and a nitinol wire, the conductive wire and the nitinol wire positioned within an electrically insulating material.

Alternatively or additionally to any of the examples above, in another example, the system may further comprise a protrusion extending inwardly from an inner surface of the distal holding section and a groove extending longitudinally in the housing of the implantable device. When the implantable device is positioned within the distal holding section, the protrusion and the groove may be configured to mate such that the implantable device is in a predefined orientation.

Alternatively or additionally to any of the examples above, in another example, the retention feature may comprise a first end affixed to an inner wall of the distal holding section and a second free end configured to engage the tine.

Alternatively or additionally to any of the examples above, in another example, the distal holding section may comprise an inflatable atraumatic distal tip.

In another example, a method of delivering an implantable leadless pacing device to a target location within a body may comprise advancing a delivery catheter into a right atrium, the delivery catheter including at least a distal holding section defining a cavity. The cavity may be configured to receive an implantable leadless pacing device. The implantable leadless pacing device may comprise a power source, circuitry operatively coupled to the power source, the circuitry configured to pace a patient's heart and/or sense electrical activity of the patient's heart, a housing at least partially enclosing the circuitry, a first electrode secured relative to and laterally offset from a longitudinal axis of the housing and exposed exterior to the housing, and a fixation mechanism secured relative to the housing. The fixation mechanism may comprise at least one tine configured to move between an elongated delivery configuration and a curved deployed configuration and radially offset from the first electrode and an ultrasound marker positioned adjacent to a distal end of the at least one tine. The method may further comprise identifying a target location using, at least in part, the ultrasound marker, positioning the distal holding section in contact with the target location, and distally advancing the implantable leadless pacing device to secure the implantable leadless pacing device to the target tissue.

Alternatively or additionally to any of the examples above, in another example, the tine may be configured to function as an electrically active element.

Alternatively or additionally to any of the examples above, in another example, the delivery catheter may further comprise a protrusion extending inwardly from an inner surface of the distal holding section and the implantable leadless pacing device may further comprise a groove extending longitudinally in the housing of the implantable device. When the implantable device is positioned within the distal holding section, the protrusion and the groove may be configured to mate such that the implantable device is in a predefined orientation.

Alternatively or additionally to any of the examples above, in another example, the distal holding section may comprise at least one retention feature configured to bias the tine to the elongated delivery configuration, the at least one retention feature may comprise a first end affixed to an inner wall of the distal holding section and a second free end configured to engage the tine.

The above summary of some embodiments is not intended to describe each disclosed embodiment or every implementation of the present disclosure. The FIGs, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which:

FIG. 2 is a side view of an example implantable leadless cardiac pacing device;

Figure 1:
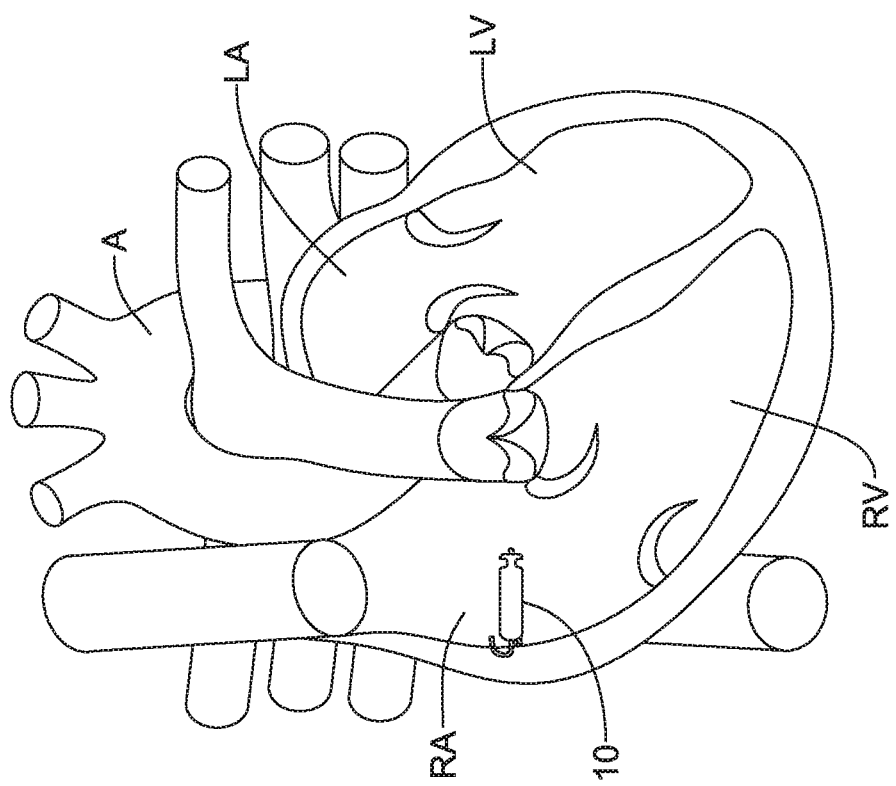
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g., a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, and into the right atrium. Other delivery approaches, such as from a radial or jugular access point are also possible. Accordingly, it may be desirable to provide delivery devices which facilitate advancement through the vasculature as well as capsules configured to fixate within the right atrium, or other chamber of the heart, or other cardiovascular location.

FIG. 1 illustrates an example implantable leadless cardiac pacing device 10 (e.g., a leadless pacemaker) implanted in a chamber of a heart H, such as the right atrium RA. The right ventricle RV, left atrium LA, left ventricle LV, and aorta A are also illustrated. Although shown implanted in the right atrium RA, it is contemplated that the implantable device 10 may alternatively be implanted in the right ventricle RV, left atrium LA, left ventricle LV, or other cardiovascular location, if desired.

A side view of the illustrative implantable device 10 is shown in FIG. 2. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12, or along another region of the housing 12. For example, housing 12 may be formed of or include an electrically conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20, which may be a cathode for example, may be capable of being positioned against or may otherwise contact the cardiac tissue of the heart H while the second electrode 22, which may be an anode for example, may be spaced away from the first electrode 20, and thus spaced away from the cardiac tissue. However, in some cases, the second electrode 22 may be spaced from the first electrode 20, but also in contact with the cardiac tissue.

In some embodiments, the first electrode 20 may be laterally offset from a central longitudinal axis 24 of the device 10 (i.e., offset in a direction perpendicular to the longitudinal axis 24). It is contemplated that the first electrode 20 may be laterally offset from the longitudinal axis 24 in any radial direction. However, in some cases, the first electrode 20 may be positioned coaxial with or centered about the longitudinal axis 24. The first electrode 20 may be formed from an iridium oxide (IrO) coated platinum iridium electrode, although other materials may be used as desired. Further, while the first electrode 20 is illustrated as extending from a surface of the device 10, it is contemplated that the first electrode 20 may be attached to or otherwise formed on a surface of the device 10. It is further contemplated that the first electrode 20 may take any shape desired and is not limited to the shape illustrated in the Figures.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition. The implantable device 10 may be configured to be used in conjunction with one or more additional medical devices, such as, but not limited to a leadless cardiac pacemaker configured to be positioned with a chamber of the heart, an implantable cardioverter-defibrillator, a subcutaneous implantable cardioverter-defibrillator, etc. It is contemplated that the additional device or leads thereof may be positioned in the same chamber of the heart H as the implantable device 10 or a different chamber of the heart H, as desired.

The implantable device 10 may include a fixation mechanism 26 proximate the distal end 16 of the housing 12 configured to attach the implantable device 10 to a tissue wall of the heart H, or otherwise anchor the implantable device 10 to the anatomy of the patient. The fixation mechanism 26 may be laterally, radially, or diametrically offset from the first electrode 20, and/or the longitudinal axis 24 of the device 10, although this is not required. As shown in FIG. 2, in some instances, the fixation mechanism 26 may include a single tine 28. In other embodiments, the fixation mechanism 26 may include one or more, or a plurality of hooks or tines 28 configured to be anchored into the cardiac tissue of the heart H to attach the implantable device 10 to a tissue wall, as shown in FIG. 1. In other instances, the fixation mechanism 26 may include one or more, or a plurality of active or passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along the longitudinal axis 24 of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis 24 of the implantable device 10 which is greater than a radial dimension of the neck portion 34 from the longitudinal axis 24 of the implantable device 10. The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g., looped) through the opening 38. The retention structure 36 may extend though the head portion 32, along the neck portion 34, and to or into the proximal end 14 of the housing 12. The docking member 30 may be configured to facilitate delivery of the implantable device 10 to the intracardiac site and/or retrieval of the implantable device 10 from the intracardiac site. Other docking members 30 are contemplated.

One aspect of the current disclosure relates to the ability to fixate the implantable device 10 in the right atrium RA. While the right atrial wall is relatively thin (e.g., in the range of 2-3 millimeters), there are some robust anatomical features within the right atrium RA that may be used for fixation, including, but not limited to, the terminal crest (Crista Terminalis). The terminal crest may have an average thickness in the range of 4-5 millimeters, or about 4.5 millimeters. The thick and/or rigid terminal crest may be used to fixate the implantable device 10 and allow for sensing and/or pacing from the right atrium RA. However other areas of increased thickness may be also be used for fixation and sensing and/or pacing. It is contemplated that the fixation mechanism 26 may be configured to target peaks in the heart H tissue whereas previous systems may target the valleys in the heart H tissue.

The fixation mechanism 26 may be formed from nitinol or other shape memory material which allows the tine 28 to be biased into a straightened configuration while positioned in a delivery catheter for advancing the device 10 to the implant location. The tine 28 may be maintained in the straightened configuration during advancement using, for example, a delivery device (e.g., sheath), as discussed in more detail herein, and allowed to assume the curved shape shown in FIG. 2 when the device 10 is deployed from the delivery device (e.g., sheath) in the desired location. In other words, the tine 28 may be advanced into the heart tissue in a straight configuration and when the implant location is confirmed, the sheath or biasing force may be removed to allow the tine 28 to bend into a curved configuration and attach the implantable device 10 to the tissue wall. In some cases, when in the curved configuration, the tine 28 may bend away from the electrode 20 such that during deployment, as the tine 28 assumes its curved configuration, the electrode 20 is drawn into contact with the tissue. In other words, as the tine 28 reverts to its curved configuration, the tine 28 may curve from the base of the tine 28 toward the tip of the tine 28 in a direction opposite the first electrode 20. While only a single tine 28 is illustrated, it should be understood that the fixation mechanism 26 may include more than one tine 28, as desired. However, in some instances, the implantable device 10 may include a single tine 28 as illustrated in FIG. 2. Further, while a proximal or base end of the tine 28 is illustrated as being affixed at or near the longitudinal axis 24 of the device, the tine 28 may be laterally offset from the longitudinal axis in any radial direction, as desired.

In some embodiments, the fixation mechanism 26 may be electrically insulated. In other embodiments, the fixation mechanism 26 may be electrically inactive (e.g., not connected to any of the electrically powered components of the implantable device 10) but also uninsulated. However, this is not required. For example, the fixation mechanism 26 may also be configured to function as an electrically active electrode in place of or in addition to one or both of the electrodes 20, 22 on the implantable device 10.

The fixation mechanism 26 may further include one or more ultrasound markers 40 positioned on or adjacent to a distal end (e.g., distal tip) of the tine 28. In some cases, the ultrasound marker 40 may be used in conjunction with an external ultrasound console in an intracardiac echocardiography (ICE) procedure. Use of intracardiac echocardiography may guide the device 10 into place as well as determine the location of the terminal crest, or other region of increased thickness in the right atrium (or other heart chamber, as desired). Other imaging or visualization techniques may be used in place of or in combination with intracardiac echocardiography including, but not limited to, fluoroscopy, transesophageal echocardiography (TEE), transthoracic echocardiography (TTE), etc.

Figure 3A:
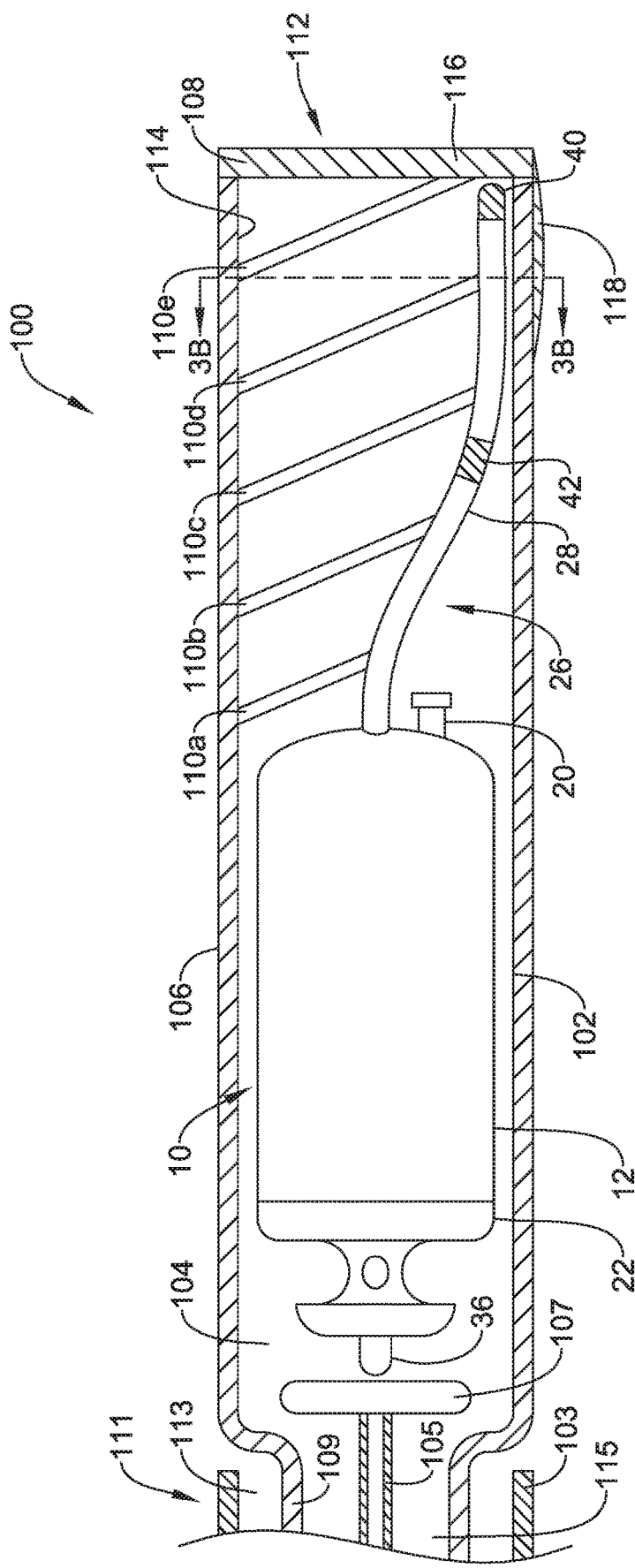
FIG. 3A is a partial cross-sectional view of a distal end region of an illustrative delivery device including the implantable leadless cardiac pacing device of FIG. 2 in a delivery configuration.

FIG. 3A is a partial cross-section of a distal portion of an illustrative delivery device 100, such as a catheter, for delivering the implantable device 10 to a suitable location within the anatomy (e.g., the heart). Some illustrative delivery devices may be found in commonly assigned US Patent Publication No. 2016/0114156, titled DELIVERY DEVICES AND METHODS FOR LEADLESS CARDIAC DEVICES, US Patent Publication No. 2016/0114157, titled DELIVERY DEVICES AND METHODS FOR LEADLESS CARDIAC DEVICES, and U.S. patent application Ser. No. 15/354,432 filed on Nov. 1, 2016, titled DELIVERY DEVICES AND METHODS FOR LEADLESS CARDIAC DEVICES, the disclosures of which are incorporated herein by reference.

The delivery device 100 may include an elongate shaft extending distally from a handle assembly. The elongate shaft may include one or more tubular members, such as an outer tubular member, an intermediate tubular member and/or an inner tubular member. For example, the elongate shaft may include an outer tubular member 103 having a proximal section (not explicitly shown) and a distal section 111. An intermediate tubular member 109 may be longitudinally slidably disposed within a lumen 113 of the outer tubular member 103. An inner tubular member 105 may be longitudinally slidably disposed within a lumen 115 of the intermediate tubular member 109. A distal portion 107 of the inner tubular member 105 may be capable of engaging the device 10, and the inner tubular member 105 may be used to "push" the device 10 out a distal holding section 102 so as to deploy and anchor device 10 within a target region (e.g., a region of the heart such as the right atrium).

The delivery device 100 may include a distal holding section 102 extending from a distal end portion of the intermediate tubular member 109 and configured to receive the implantable device 10 within a cavity 104 thereof. In some instances, the distal holding section 102 may have a sufficient length to receive the entire length of the implantable device 10, including the housing 12 and the elongated fixation tine 28 in its elongated delivery configuration. The holding section 102 may slidably receive the implantable device 10 within the cavity 104, and may include a distal opening 112 for slidable insertion and/or extraction of the implantable device 10 into and/or out of the cavity 104.

Figure 6:
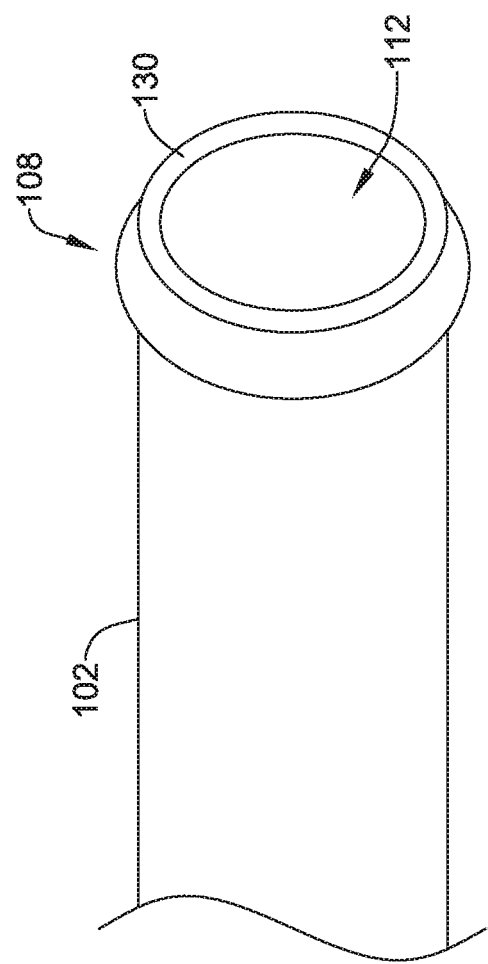
FIG. 6 is a perspective view of a distal end of an illustrative delivery catheter having an atraumatic tip.

The distal holding section 102 may include a body portion 106 and a distal tip portion 108 that may be, for example, configured to be atraumatic to anatomy, such as a bumper tip. For example, as the delivery catheter is navigated through the anatomy, the distal tip 108 may come into contact with an anatomical structure. Additionally, when the delivery catheter is used to deliver the implantable device 10, the tip 108 of the delivery device 100 will likely come into contact with tissue adjacent the target site (e.g., cardiac tissue of the heart). A hard distal tip may injure a vessel wall or cardiac tissue. As such, it may be desirable to provide the delivery device 100 with a softer distal tip 108 that can be introduced into the anatomy and come into contact with anatomy adjacent the target site without causing unnecessary trauma. In some embodiments, the distal tip 108 may include an inflatable balloon 130, as shown in FIG. 6. Once in the desired heart chamber (or other target location), the balloon 130 may be inflated with fluid, such as but not limited to saline, to increase the surface area of the distal tip 108 in contact with the target tissue (e.g., cardiac tissue). In some instances, the inflated balloon 130 may be an annular balloon surrounding the distal opening 112 of the distal holding section 102. This may distribute the force exerted by the distal tip 108 over a larger surface area (relative to the distal tip 108 in the uninflated configuration), thus reducing the pressure on the tissue to reduce the likelihood of perforation or other trauma.

In some cases, the distal tip 108 may include a material that has a durometer that is less than the durometer of the material of the body portion 106. In some particular embodiments, the durometer of the material used in the distal tip 108 may be in the range of about 5 Shore D to about 70 Shore D, or for example, in the range of about 25 Shore D to about 65 Shore D. Additionally, the distal tip 108 may include a shape or structure that may make it less traumatic to tissue. For example, the distal tip 108 may have a distal surface, such as a tissue contacting surface, that is rounded or includes a curvature configured to be more atraumatic to tissue.

In some embodiments, all or a portion of the distal holding section 102 may include an inner surface that may be configured to resist getting caught on the fixation mechanism 26, such as the one or more, or a plurality of hooks or tines 28 on the device 10. For example, the distal holding section 102 may include an inner layer or coating of harder or more lubricious material that resists force applied by the fixation mechanism 26 onto the inner surface of the distal holding section 102. For example, the distal holding section 102 may include a multi-layered structure, and an inner layer may be made of a material that is harder than an outer layer.

The distal holding section 102 may further include one or more, or a plurality of retention features 110a, 110b, 110c, 110d, 110e (collectively, 110) within the cavity 104 configured to hold the tine 28 in an elongated or generally straight configuration during delivery of the device 10. While the distal holding section 102 is illustrated as including five retention features 110, it is contemplated that the distal holding section 102 may include any number of retention features 110 such a single retention feature, two or more, three or more, four or more, or five or more retention features 110. In some instances, a plurality of retention features 110 may be longitudinally arranged along the inner surface 114 of the distal holding section 102. However, it is further contemplated that the retention features 110 need not be arranged in a linear row. In some cases, there may be multiple rows, a staggered arrangement, or arranged in no specific pattern, as desired. In some embodiments, the retention features 110 may be a plurality of flexible fingers extending (e.g., radially inward) from an inner surface 114 of the distal holding section 102. The retention features 110 may include a base portion secured to or otherwise fixed at the inner surface 114. The retention features 110 may extend from the base portion to a free end 134 (see, for example, FIG. 3B) configured to engage the tine 26. In some instances, the retention feature 110 may be a looped structure having two base portions secured to or otherwise fixed to the inner surface 114 with a loop defining the free end. In some cases, the retention features 110 may be thin filament-like structures, while in other cases the retention features 110 may be wide strip-like structures. These are just examples.

In some instances, the retention features 110 may be angled in a distal direction from the base portion of the retention features 110 toward the free end of the retention features 110. In other instances, the retention features 110 may be angled in a proximal direction from the base portion of the retention features 110 toward the free end of the retention features 110. Thus, the retention features 110 may be arranged at an oblique angle to the central longitudinal axis of the distal holding section 102 and/or inner surface of the distal holding section 102 in some instances. However, in other instances, the retention features 110 may be arranged perpendicular to the central longitudinal axis of the distal holding section 102 and/or inner surface of the distal holding section 102.

The retention features 110 may be sufficiently flexible to deflect from a first configuration when the implantable device 10 is not disposed within the cavity 104 to a second configuration when the implantable device 10 is disposed within the cavity 104. The retention features 110 may be angled distally in both the first and second configurations, if desired.

The retention features 110 may extend across the cavity 104 of the distal holding section 102 to engage a portion of the implantable device 10. In some instances, the retention features 110 may extend from the inner wall 114 across the cavity 104 greater than one-half the diameter of the cavity 104. In some instances, the retention features 110 may extend from the inner wall 114 substantially across the cavity 104 to the opposing side of the inner wall 114 when not deflected by the implantable device 10. In some instances, the retention features 110 may extend from the inner wall 114 across the cavity 104 to the opposing side of the inner wall 114 when not deflected by the implantable device 10. In some instances, one or more of the retention features 110 may have a different length than one or more of the other retention features 110. For example, one or more of the retention features 110 may have a length greater than one or more of the more proximally positioned retention features 110. In some instances, the length of each successive retention feature 110, or subset thereof, may increase in a distal direction.

Figure 4:
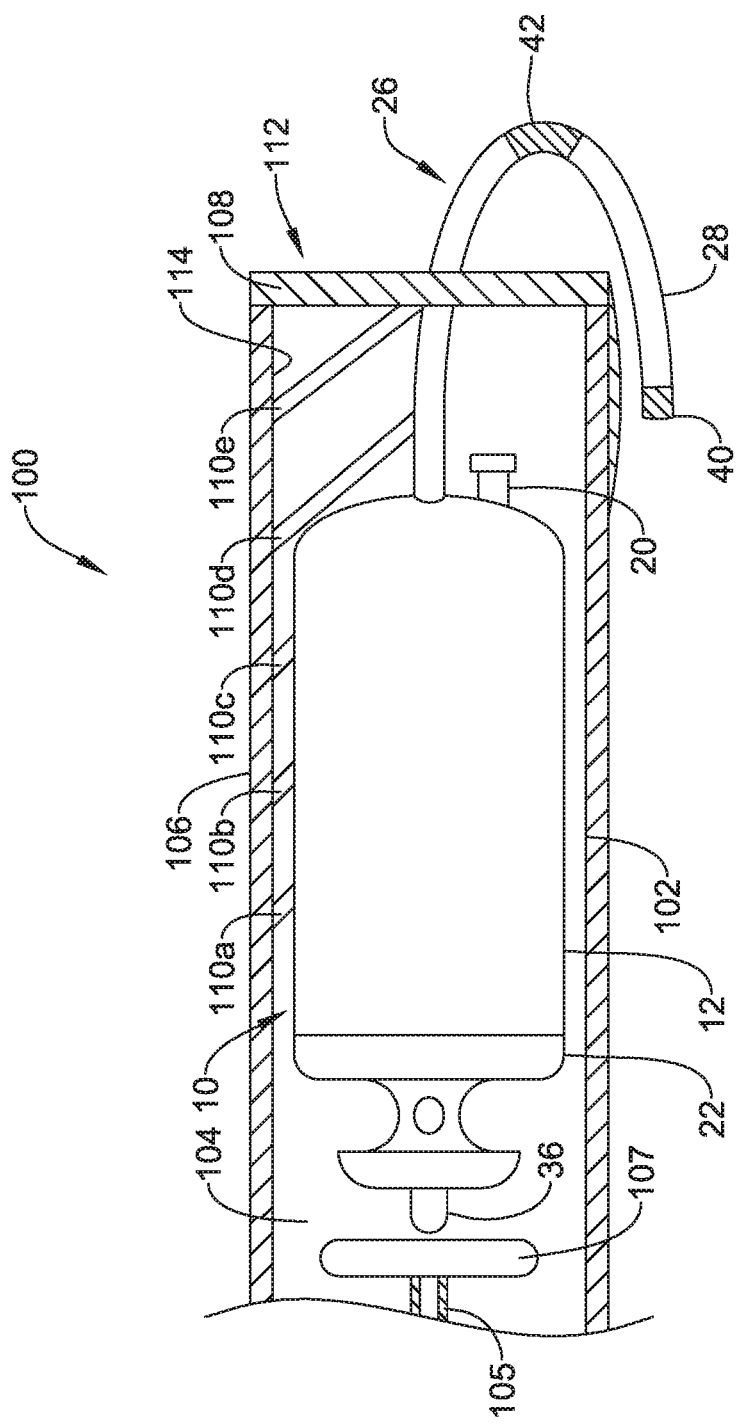
FIG. 4 is a partial cross-sectional view of a distal end region of an illustrative delivery device including the implantable leadless cardiac pacing device of FIG. 2 in a partially deployed configuration.

The retention features 110 may be configured to exert a biasing force on the tine 28. For example, the retention features 110 may exert a biasing force on the tine 28 to press the tine 28 against the inner surface 114 of the distal holding section 102 opposite the base of the retention features 110. In some cases, the retention features 110 may be formed from silicone. However, it is contemplated that any material that may be configured to move between a first configuration which exerts a biasing force on the tine 28 and a second configuration which allows for the distal advancement of the device 10 out of the distal opening 112 for delivery of the device 10. For example, the retention features 110 may be biased towards the configuration shown in FIG. 3A to maintain the fixation mechanism 26 in a delivery configuration. However, the retention features 110 may be deflected by distal movement of the implantable device 10, as shown in FIG. 4, which illustrates a partial cross-section of a distal portion of the illustrative delivery device 100 with the implantable device in a partially deployed configuration. While the retention features 110 have been described as a plurality of flexible "fingers", it is contemplated that the retention features 110 may be any structure configured to hold the fixation mechanism 26 in the elongated undeployed or delivery configuration.

The distal holding section 102 may further include one or more radiopaque markers 116, 118. For example, a radiopaque marker 116 may be positioned at or adjacent to the distal tip 108 and a radiopaque marker 118 may additionally or alternatively be positioned adjacent to the fixation mechanism 26, when the fixation mechanism 26 is in the delivery configuration, as shown in FIG. 3A. In some cases, the radiopaque marker 116 may be a ring positioned at the distal tip 108, although other shapes and configurations may be used. The radiopaque marker 118 may be a generally linear strut or strip extending longitudinally along a longitudinal length of the distal holding section 102 and configured to identify the location of the fixation mechanism 26 and its rotational position within the cavity 104.

Figure 3B:
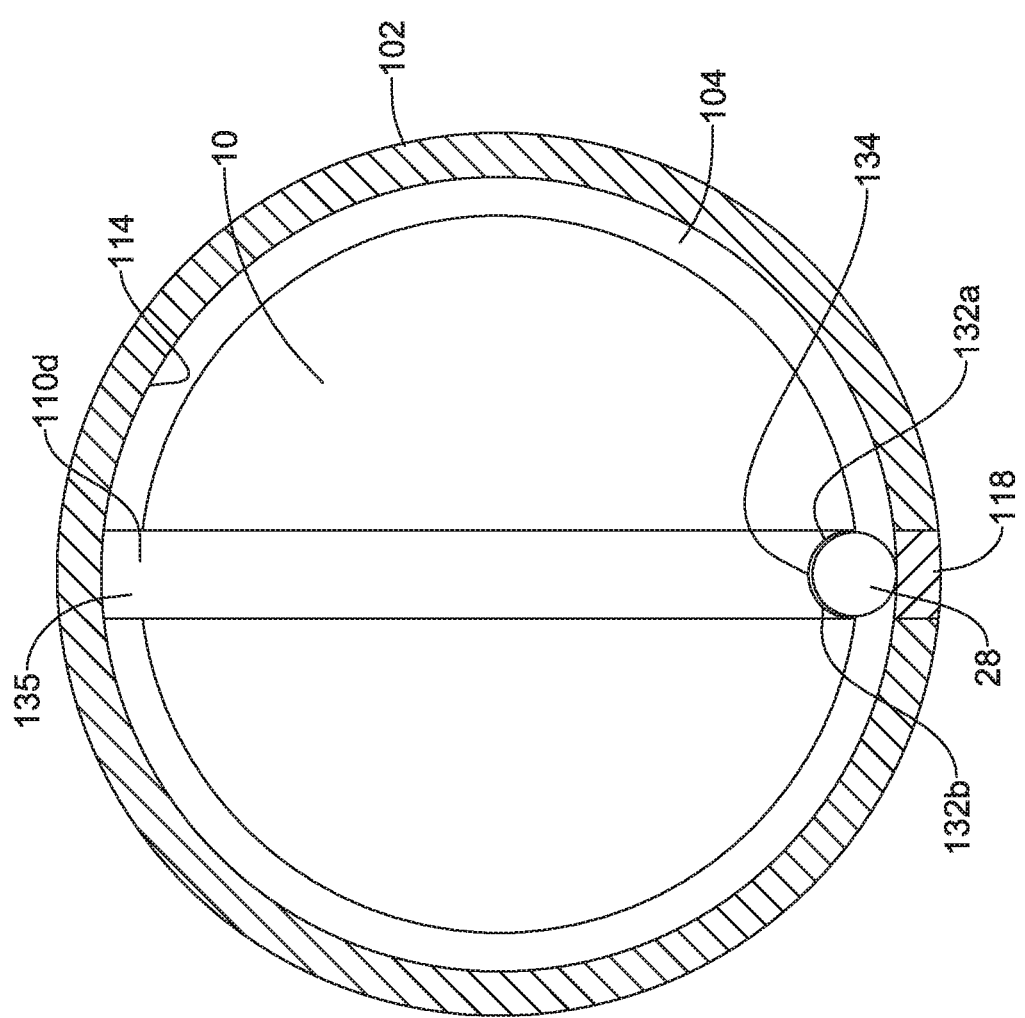
FIG. 3B is a cross-sectional view of the illustrative distal end region of FIG. 3A, taken at line 3B-3B of FIG. 3A.

FIG. 3B illustrates a cross-sectional view of the illustrative distal holding section 102 including the implantable device 10, taken at line 3B-3B in FIG. 3A. As can be seen in FIG. 3B, the retention features 110 may extend from an attached, base end 135 at the inner surface 114 to a free end 134 configured to hold the fixation mechanism 26 in an elongated delivery configuration. The free end 134 may include a surface configured to cradle or generally conform to an outer surface of the fixation mechanism 26, which may reduce unintentional radially and/or circumferential movement of the fixation mechanism 26. For example, the free end 134 may include a concave surface or other recessed region having a first arm 132a positioned on a first side of the tine 28 and a second arm 132b positioned on a second side of the tine 28. As can be seen in FIG. 3B, the retention features 110 may be configured to align or generally align the tine 28 with the radiopaque marker 118. This may help to guide the placement of the fixation mechanism 26 and/or facilitate rehousing of the device 10 within the distal holding section 102.

While not explicitly shown, the distal holding section 102 may further include an outlet extending along the longitudinal axis thereof for the injection of a contrast agent, or other fluid. In some cases, the outlet may be positioned to provide a concentrated area of contrast in line with or adjacent to where a distal end of the tine 28 exits the distal holding section 102

As described above, the fixation mechanism 26 may be formed from a shape memory material, such as, but not limited to, nitinol. The fixation mechanism 26 may be formed such that the "remembered" shape is the generally curved deployed configuration illustrated in FIG. 2. As the fixation mechanism 26 is loaded into the distal holding section 102, the tine 28 of the fixation mechanism 26 may be biased (e.g., by applying an external force thereto) into a generally straightened delivery configuration, shown in FIG. 3A. When loading the implantable device 10 into the cavity 104 of the distal holding section 102, the tine 28 may be aligned with the radiopaque marker 118 with the tine 28 pressed against the inner surface 114 where the radiopaque marker 118 is positioned, while the retention features 110 hold the tine 28 in a fixed arrangement. In other words, the retention feature(s) 110 may press the tine 28 against the annular wall of the distal holding section 102 at generally the same circumferential location as the radiopaque marker 118 is located, thus permitting the radiopaque marker 118 to act as an indicator of the circumferential location of the tine 28 and the trajectory of the tine 28 when deployed from the distal holding section 102. During delivery of the device 10, the orientation of the fixation mechanism 26 can be monitored via the radiopaque marker 118 such that the operator can determine which direction the tine 28 will curve toward when deployed from the distal opening 112 of the distal holding section 102. It is further contemplated that the device 10 may be loaded such that when the device 10 is deployed a distal portion of the curved tine 28 is in line with and/or parallel to the radiopaque marker 118, as shown in FIG. 4, with the distal tip of the tine located radially outward of the radiopaque marker 118. In some instances, the curved tine 28 may be in a plane parallel to the central longitudinal axis of the housing 12 which passes through the central longitudinal axis of the housing 12 and the radiopaque marker 118. In some cases, one or more additional radiopaque markers 42 may be provided anywhere along the length of the tine 28 to further facilitate visualization of the fixation mechanism 26.

Figure 5:
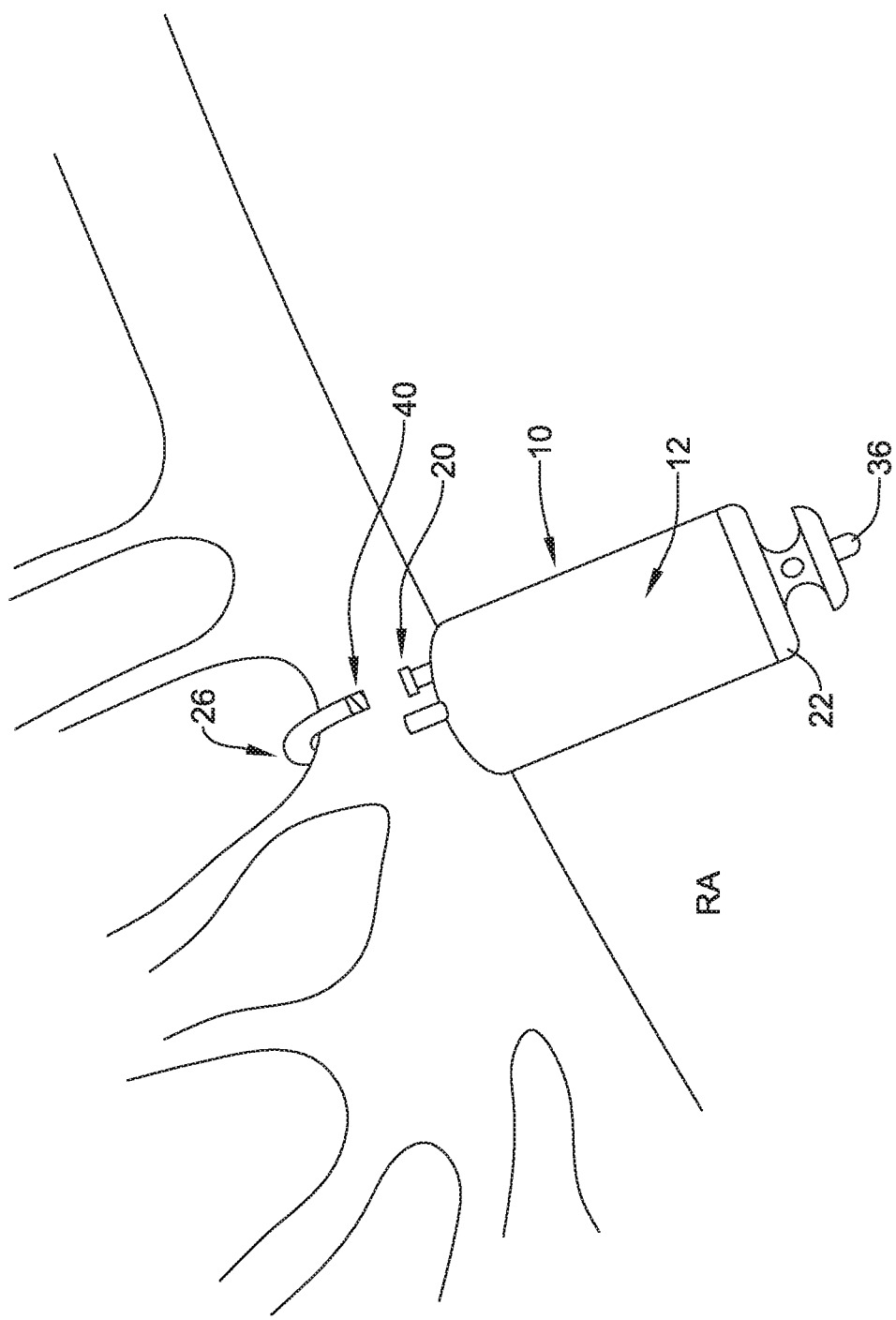
FIG. 5 is a partial cut-away view of a heart with the illustrative implantable leadless cardiac pacing device of FIG. 2 fixated within the heart.

After the delivery device 100 has been advanced to the target location, the implantable device 10 may be deployed distally from the distal opening 112. As described above, in some cases, the target location may be the terminal crest, or other region of increased wall thickness, in the right atrium RA of the heart. The distal tip 108 may be positioned against the tissue at the target location. As the device 10 is advanced distally from the distal holding section 102 and into the tissue, the distal tip of the tine 28 may penetrate into tissue at the terminal crest as the tine 28 and the tine 28 may begin to revert back to its curved shape. Once the device 10 has been sufficiently deployed from the distal holding section 104, the tine 28 may return to its remembered or curved shape, with the curved portion of the tine 28 passing through the tissue. This may cause the fixation mechanism 26 to loop back on itself, forming a hook configuration. As it resumes the curved shape, the fixation mechanism 26 may fixate in the tissue and pull the electrode 20 into contact with the tissue, as shown in FIG. 5, which illustrates a close up partial cut-away view of the implantable device 10 fixated within the terminal crest of the right atrium RA. As noted above, the terminal crest is just one illustrative implant location and is not intended to be limiting. In some instances, the tine 28 may exit the heart and re-enter the heart. In other words, the tine 28 may extend through an entire thickness of the heart wall before curving back on itself to re-enter the heart wall.

In some instances, it may be desirable or necessary to recapture the implantable device 10 within the distal holding section 102. For example, the implantable device 10 may need to be repositioned after it has been deployed into the tissue. In such an instance, the implantable device 10 is proximally retracted into the distal holding section 102 for retrieval, for example. However, it may be desirable to recapture the device 10 in a manner that aligns the fixation mechanism 26 with the location of the radiopaque marker 118 in a predictable and repeatable manner. For example, the fixation mechanism 26 may be radially aligned with the radiopaque marker 118 such that its radial location is visible to physician under fluoroscopy. In some cases, the retention features 110 may hold a distal end region of the tine 28 against the inner surface 114 of the distal holding section 102 such that it is radially and/or circumferentially aligned with the radiopaque marker 118. It is contemplated that a proximal portion of the implantable device 10 and a distal portion of the distal holding section 102 may be "keyed" to house and/or recapture the device 10 into a repeatable location, as will be described in more detail with respect to FIGS. 8 and 9. For example, the proximal portion (or the entire length) of the implantable device 10 may include a groove configured to engage a mating protrusion in the distal holding section 102. The reverse configuration is also contemplated in which the implantable device 10 may include a protrusion configured to engage a mating recess in the distal holding section 102. Other "keying" features may also be utilized, such as but not limited to an Allen wrench shaped housing 12 on the implantable device 10 and a mating distal holding section, or other flattened surface on the implantable device 10 configured to mate with a similar flattened surface of the distal holding section 102.

Figure 7:
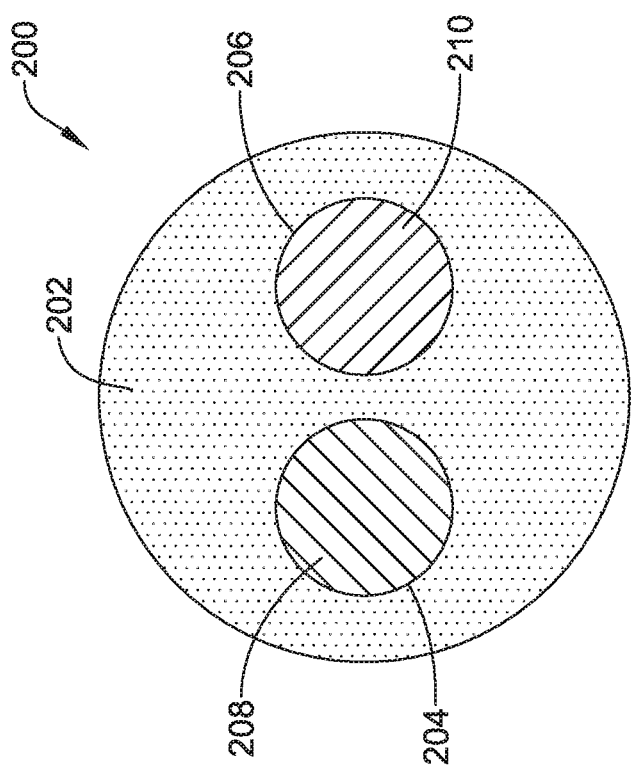
FIG. 7 is a cross-sectional view of another illustrative fixation element for use with an implantable leadless cardiac pacing device.

In some embodiments, the fixation mechanism 26 may be electrically insulated or electrically inactive. However, this is not required. For example, the fixation mechanism 26 may also be configured to function as an electrically active electrode in place of or in addition to one or both of the electrodes 20, 22 on the implantable device 10. FIG. 7 illustrates a cross-section of an illustrative tine 200 for use in a fixation mechanism, such as the fixation mechanism 26 described herein, that includes both shape memory retention features as well as an electrically active electrode. The tine 200 may be formed from an electrically insulating material 202 including, but not limited to silicone, polyvinylidene fluoride (PVDF), polyethylene, etc. The tine 200 may include at least a first lumen 204 and a second lumen 206. A conductive coil and/or wire 208 maybe positioned within the first lumen 204 to function as an electrode and a nitinol wire 210 may be positioned within the second lumen 206 to function as the retention feature. Alternatively, instead of forming or otherwise providing lumens 204, 206 within the insulating material 202, the insulating material 202 may be molded over or formed around the conductive element 208 and the nitinol wire 210.

Figure 8:
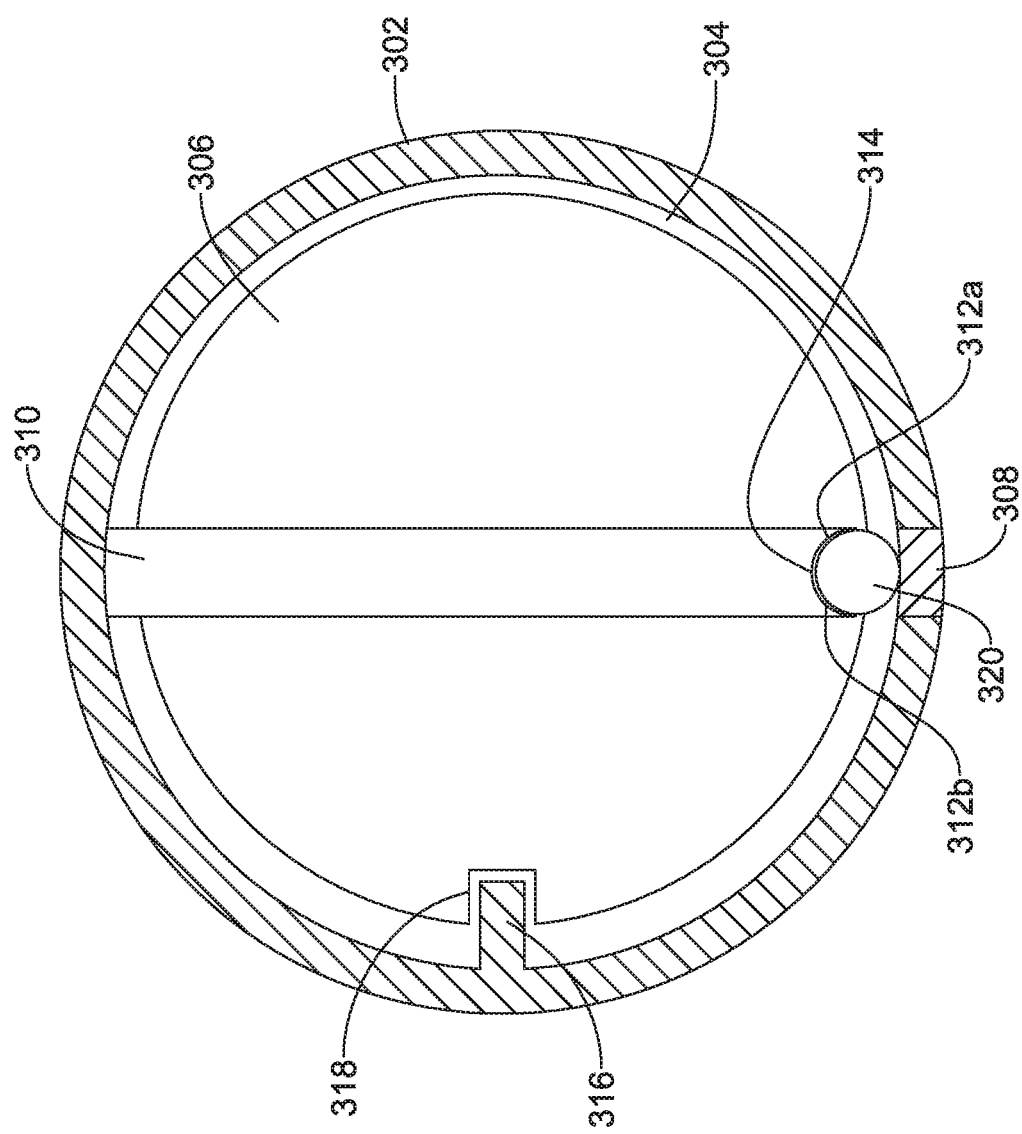
FIG. 8 is another illustrative cross-sectional view of another illustrative delivery device including an illustrative implantable leadless cardiac pacing device.

FIG. 8 illustrates a cross-sectional view of an illustrative distal holding section 302 including an implantable device 306 positioned within a cavity 304 of the distal holding section 302. The distal holding section 302 may be similar in form and function to the distal holding section 102 described herein. Similarly, the implantable device 306 may be similar in form and function to the implantable device 10 described herein. The distal holding section 302 may include one or more retention features 310 configured to maintain a fixation mechanism 320 of the device 306 in an elongated delivery configuration against an inner surface of the distal holding section 302. The retention features 310 may be similar in form and function to the retention features 110 described above. For example, the retention features 310 may extend from a first base end affixed to an inner surface of the distal holding section 302 to a free end 314 configured to engage the fixation mechanism 320. In some cases, the free end 314 may include a surface configured to cradle or generally conform to an outer surface of the fixation mechanism 320, although this is not required. For example, the free end 314 may include a concave surface or other recessed region having a first arm 312a positioned on a first side of the fixation mechanism 320 and a second arm 312b positioned on a second side of the fixation mechanism 320. As can be seen in FIG. 8, the retention features 310 may be configured to align or generally align the fixation mechanism 320 with a radiopaque marker 308. This may help to guide the placement of the fixation 320 and/or facilitate rehousing of the device 306 within the distal holding section 302.

In some embodiments, the implantable device 306 may include a groove or recess 318 extending longitudinally along a side of the housing of the device 306. The recess 318 may be configured to be slidably engaged with a mating protrusion 316 extending inwardly from an inner surface of the distal holding section 302. The protrusion 316 and recess 318 may be sized and shaped such that the implantable device 306 must be loaded into the cavity 304 in a predefined rotational orientation. The predefined orientation may be chosen such that the fixation mechanism 320 is radially and/or circumferentially aligned with the radiopaque marker 308. This may allow the device 306 to be recaptured within the cavity 304 in a manner that aligns the fixation mechanism 320 with the location of the radiopaque marker 308 in a predictable and repeatable manner. While the protrusion 316 and mating recess 318 are illustrated as having a generally square or rectangular cross-sectional shape, it is contemplated that the protrusion 316 and/or recess 318 may take any shape desired, such as, but not limited to, round, I-beam, triangular, oblong, polygonal, etc.

Figure 9:
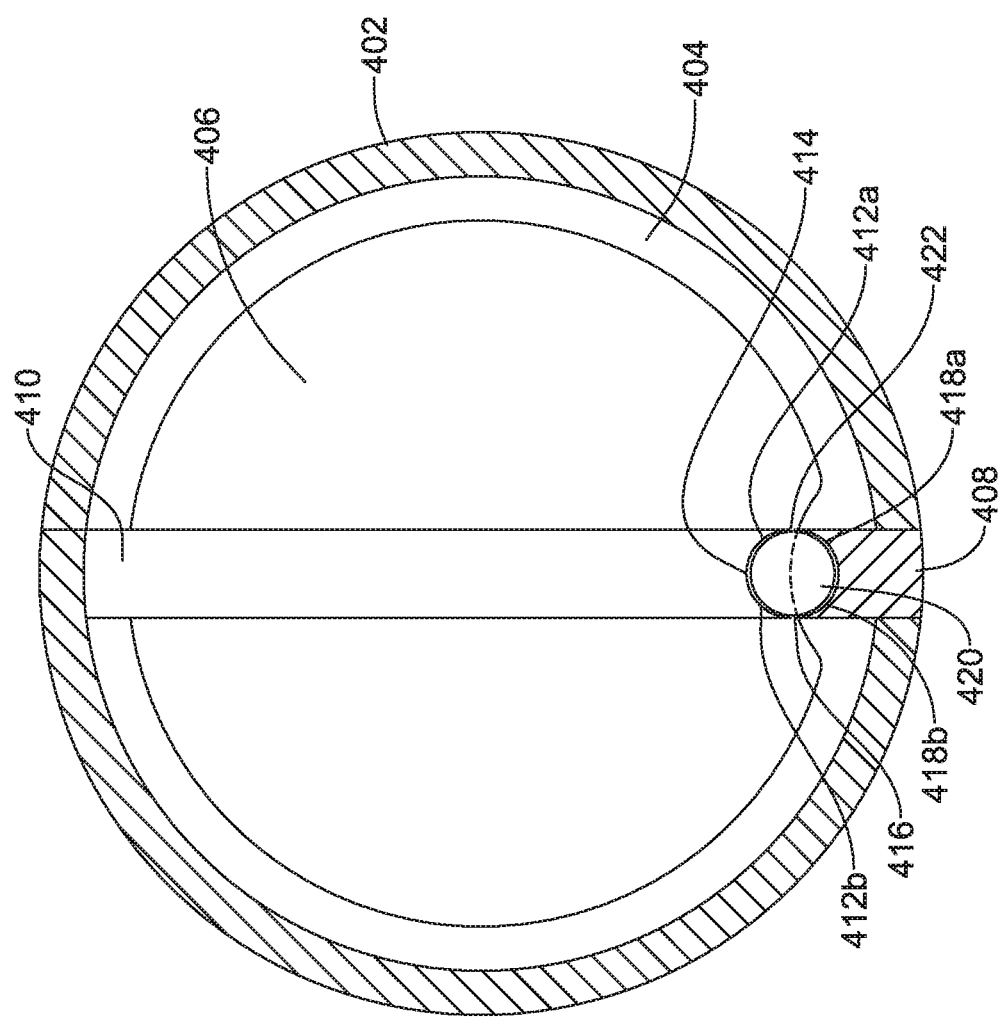
FIG. 9 is another illustrative cross-sectional view of another illustrative delivery device including an illustrative implantable leadless cardiac pacing device.

FIG. 9 illustrates a cross-sectional view of an illustrative distal holding section 402 including an implantable device 406 positioned within a cavity 404 of the distal holding section 402. The distal holding section 402 may be similar in form and function to the distal holding section 102 described herein. Similarly, the implantable device 406 may be similar in form and function to the implantable device 10 described herein. The distal holding section 402 may include one or more retention features 410 configured to maintain a fixation mechanism 420 of the device 406 in an elongated delivery configuration. The retention features 410 may be similar in form and function to the retention features 110 described above. For example, the retention features 410 may extend from a first base end affixed to an inner surface of the distal holding section 402 to a free end 414 configured to engage the fixation mechanism 420. In some cases, the free end 414 may include a surface configured to cradle or generally conform to an outer surface 422 of the fixation mechanism 420, although this is not required. For example, the free end 414 may include a concave surface or recessed region having a first arm 412a positioned on a first side of the fixation mechanism 420 and a second arm 412b positioned on a second side of the fixation mechanism 420. As can be seen in FIG. 9, the retention features 410 may be configured to align or generally align the fixation mechanism 420 with a protrusion 408 extending inwardly from an inner surface of the distal holding section 402. In some cases, the protrusion 408 may be formed from a radiopaque material. This may help to guide the placement of the fixation 420 and/or facilitate rehousing of the device 406 within the distal holding section 402.

The protrusion 408 may have a radially inwardly directed surface configured to cradle or generally conform to an outer surface 422 of the fixation mechanism 420, although this is not required. For example, the free end of the protrusion 408 may include a concave surface or recessed region having a first arm 418a positioned on a first side of the fixation mechanism 420 and a second arm 418b positioned on a second side of the fixation mechanism 420. The protrusion 408 may have a free end or radially inwardly facing surface having a generally concave surface, although this is not required. The implantable device 406 (e.g., the housing of the implantable device 406) may include a groove or recess, or other mating features 416 extending longitudinally along a side thereof. The recess 416 may be configured to be slidably engaged with the protrusion 408 extending inwardly from an inner surface of the distal holding section 402. The protrusion 408 and recess 416 may be sized and shaped such that the implantable device 406 must be loaded into the cavity 404 in a predefined rotational orientation. The predefined orientation may be chosen such that the fixation mechanism 420 is radially and/or circumferentially aligned with a radiopaque marker, such as the protrusion 408. This may allow the device 406 to be recaptured within the cavity 404 in a manner that aligns the fixation mechanism 420 with the location of the radiopaque marker in a predictable and repeatable manner. While the protrusion 408 and mating recess 416 are illustrated as having a generally concave, square or rectangular cross-sectional shape, it is contemplated that the protrusion 408 and/or recess 416 may take any shape desired, such as, but not limited to, round, I-beam, triangular, oblong, polygonal, etc.

The materials that can be used for the various components of the implantable leadless cardiac pacemaker, such as the implantable device 10 (and/or other device structures including the various fixation mechanisms, delivery devices and components thereof 26, 100 200 disclosed herein) and the various members disclosed herein may include those commonly associated with medical devices. For simplicity purposes, the following discussion makes reference to the implantable device 10 and components of thereof. However, this is not intended to limit the devices and methods described herein, as the discussion may be applied to other similar delivery systems and/or components of delivery systems or devices disclosed herein.

The implantable device 10 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; platinum; iridium; palladium; tungsten; titanium; combinations thereof; and the like; or any other suitable material.

In at least some embodiments, portions or all of the implantable device 10 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the implantable device 10 in determining its location and orientation. Some examples of radiopaque materials can include, but are not limited to, gold, platinum, palladium, tantalum, tungsten alloy, polymer material loaded with a radiopaque filler (e.g., barium sulfate, bismuth subcarbonate, bismuth oxychloride, etc.), and the like. Additionally, other radiopaque marker bands and/or coils may also be incorporated into the design of the implantable device 10 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable leadless pacing device comprising:
   a power source;
   circuitry operatively coupled to the power source, the circuitry configured to pace a patient's heart and/or sense electrical activity of the patient's heart;
   a housing at least partially enclosing the circuitry;
   a first electrode secured to and offset from a central longitudinal axis of the housing, the first electrode exposed exterior to the housing and extending distal of the housing; and
   a fixation mechanism secured relative to the housing, the fixation mechanism comprising a tine configured to move between an elongated delivery configuration with a free end of the tine pointed distally and a curved deployed configuration and radially offset from the first electrode;
   wherein a proximal end of the tine is affixed to the housing at a central longitudinal axis of the housing and the first electrode is diametrically spaced from the tine;
   wherein when in the curved deployed configuration, the tine is configured to curve away from the first electrode with the free end of the tine located proximal of a distalmost extent of the tine.

2. The implantable leadless pacing device of claim 1, further comprising an ultrasound marker positioned adjacent to a distal end of the tine.

3. The implantable leadless pacing device of claim 1, wherein the tine is configured to function as an electrically active element.

4. An implantable leadless pacing device and delivery system comprising:

the implantable leadless pacing device of claim 1; and
a catheter configured to deliver the implantable leadless pacing device to a target location, the catheter comprising:
   a distal holding section defining a cavity, the cavity configured to receive the implantable leadless pacing device.

5. The system of claim 4, further comprising an ultrasound marker positioned adjacent to a distal end of the tine.

6. The system of claim 4, wherein the tine is configured to be in the elongated delivery configuration when the implantable leadless pacing device is disposed within the cavity of the distal holding section.

7. The system of claim 4, further comprising a radiopaque marker extending longitudinally along a wall of the distal holding section.

8. The system of claim 7, wherein the tine is aligned with the radiopaque marker in the elongated delivery configuration.

9. The system of claim 4, further comprising a retention feature disposed within a cavity of the distal holding section, the retention feature configured to bias the tine into the elongated delivery configuration.

10. The system of claim 9, wherein the retention feature comprises a plurality of flexible fingers extending from an inner surface of the distal holding section.

11. The system of claim 9, wherein the retention feature comprises a first end affixed to an inner wall of the distal holding section and a second free end configured to engage the tine.

12. The system of claim 4, wherein the tine is configured to function as an electrically active element.

13. The system of claim 4, wherein the tine comprises a conductive wire and a nitinol wire, the conductive wire and the nitinol wire positioned within an electrically insulating material.

14. The system of claim 4, further comprising:
   a protrusion extending inwardly from an inner surface of the distal holding section; and
   a groove extending longitudinally in the housing of the implantable leadless pacing device;
   wherein when the implantable leadless pacing device is positioned within the distal holding section, the protrusion and the groove are configured to mate such that the implantable leadless pacing device is in a predefined orientation.

15. The system of claim 4, wherein the distal holding section comprises an inflatable atraumatic distal tip.

16. An implantable leadless pacing delivery system comprising:
   an implantable leadless pacing device comprising:
      a power source;
      circuitry operatively coupled to the power source, the circuitry configured to pace a patient's heart and/or sense electrical activity of the patient's heart;
      a housing at least partially enclosing the circuitry;
      a first electrode secured to and exposed exterior to the housing;
      a fixation mechanism secured relative to the housing, the fixation mechanism comprising a tine configured to move between an elongated delivery configuration and a curved deployed configuration and radially offset from the first electrode; and
   a catheter configured to deliver the implantable leadless pacing device to a target location, the catheter comprising:

a distal holding section including a body and a distal tip, the body defining a cavity, the cavity configured to receive the implantable leadless pacing device, a retention feature disposed within the cavity, the retention feature configured to bias the tine into the elongated delivery configuration, wherein the retention feature comprises a first end affixed to an inner wall of the body at a position spaced apart proximally from the distal tip, the retention feature having a second free end configured to contact the tine.

17. The system of claim 16, wherein when in the curved deployed configuration, the tine is configured to curve away from the first electrode.

18. The system of claim 16, wherein the tine is configured to function as an electrically active element.

19. An implantable leadless pacing device comprising:

a power source;

circuitry operatively coupled to the power source, the circuitry configured to pace a patient's heart and/or sense electrical activity of the patient's heart;

a housing at least partially enclosing the circuitry;

a first electrode secured to and offset from a central longitudinal axis of the housing, the first electrode exposed exterior to the housing and extending distal of the housing; and a fixation mechanism secured relative to the housing, the fixation mechanism consisting of a single tine configured to move between an elongated delivery configuration with a free end of the tine pointed distally and a curved deployed configuration and radially offset from the first electrode;

wherein a proximal end of the single tine is affixed to the housing at a central longitudinal axis of the housing and the first electrode is diametrically spaced from the single tine;

wherein when in the curved deployed configuration, the single tine is configured to curve away from the first electrode with the free end of the single tine located proximal of a distalmost extent of the single tine.

* * * * *